(12) United States Patent
Corma Canós et al.

(10) Patent No.: US 7,378,059 B2
(45) Date of Patent: May 27, 2008

(54) DOWNFLOW TEST UNIT FOR THE STUDY OF CATALYSTS IN SHORT CONTACT TIME REACTIONS BETWEEN THE CATALYST AND THE REAGENTS

(75) Inventors: Avelino Corma Canós, Valencia (ES); Laurent L. A. Sauvanaud, Valencia (ES); Francisco V. Melo Faus, Valencia (ES)

(73) Assignees: Consejo Superior De Investigaciones Cientificas, Madrid (ES); Universidad Politecnica De Valencia, Valencia (ES)

( * ) Notice: Subject to any disclaimer, the term of this patent is extended or adjusted under 35 U.S.C. 154(b) by 905 days.

(21) Appl. No.: 10/850,356

(22) Filed: May 20, 2004

(65) Prior Publication Data

US 2005/0003552 A1 Jan. 6, 2005

Related U.S. Application Data

(63) Continuation of application No. PCT/ES02/00535, filed on Nov. 15, 2002.

(30) Foreign Application Priority Data

Nov. 20, 2001 (ES) ................. 200102670

(51) Int. Cl.
*G01N 31/10* (2006.01)
*B01J 8/12* (2006.01)
*B01J 19/30* (2006.01)
*C10G 11/14* (2006.01)
*C10G 11/18* (2006.01)

(52) U.S. Cl. ............ 422/130; 422/129; 422/144; 422/145; 422/147; 422/213; 436/37; 208/113

(58) Field of Classification Search ........... 422/129, 422/130, 144–145, 147, 213, 232, 234–235; 436/37; 208/113
See application file for complete search history.

(56) References Cited

U.S. PATENT DOCUMENTS 2,550,727 A * 5/1951 Shimp .................. 208/165

(Continued)

FOREIGN PATENT DOCUMENTS

JP 10-251664 * 9/1998

OTHER PUBLICATIONS

Marshall, J. A. et al, Industrial and Engineering Chemistry 1953, 45, 1603-1608.*

(Continued)

*Primary Examiner*—Arlen Soderquist
(74) *Attorney, Agent, or Firm*—Klauber & Jackson

(57) ABSTRACT

A test unit for the study of catalysts in short contact time reactions between a catalyst and at least one reagent, with a down transported flow reactor (4), with a load inlet (13, 13a, 13b) and a discharge outlet (14) linked with an admission inlet (15) to an upper chamber (39) of a separator (5) internally divided into an upper chamber (39) and a lower chamber (41) by a porous element (40) that is permeable to gases and impermeable to solid particles of catalyst, and a first preheater (1) provided with an outlet (2, 2a) connected with the inlet (13, 13a, 13b) of the reactor (4) via a load duct (42) in such a way that arranged between the outlet (2, 2a) and the load inlet (13, 13a, 13b) are some obturator means (3, 3a) in which the catalyst is heated to a desired temperature before they are loaded into the reactor (4).

35 Claims, 5 Drawing Sheets

U.S. PATENT DOCUMENTS

| | | | |
|---|---|---|---|
| 3,238,121 A * | 3/1966 | Parkin | 208/165 |
| 4,119,526 A * | 10/1978 | Peters et al. | 208/64 |
| 4,167,553 A * | 9/1979 | Persico et al. | 422/216 |
| 4,385,985 A * | 5/1983 | Gross et al. | 208/113 |
| 4,514,285 A * | 4/1985 | Niccum et al. | 208/148 |
| 4,693,808 A * | 9/1987 | Dewitz | 208/113 |
| 4,695,370 A * | 9/1987 | Galtier et al. | 208/113 |
| 4,948,569 A * | 8/1990 | Martin et al. | 422/142 |
| 4,985,136 A | 1/1991 | Bartholic | |
| 5,102,628 A | 4/1992 | De Lasa | |
| 5,468,369 A * | 11/1995 | Muldowney | 208/113 |
| 5,582,712 A * | 12/1996 | Zinke et al. | 208/113 |
| 5,660,716 A * | 8/1997 | Bourgogne et al. | 208/163 |
| 5,843,377 A * | 12/1998 | Fandel et al. | 422/144 |
| 5,948,240 A * | 9/1999 | Mulvaney et al. | 208/79 |
| 6,069,012 A | 5/2000 | Kayser | |
| 6,143,253 A * | 11/2000 | Radcliffe et al. | 422/145 |

OTHER PUBLICATIONS

ASTM—Designation: D 3907-86—Standard Method for Testing Fluid Cracking Catalysts by Microactivity Test, pp. 661-668.

Helmsing, MP, etal., Short Contact Time Experiments in a Novel Benchscale FCC Riser Reactor, 1996, Chem Eng. Sci., 51 pp. 3039-3044.

* cited by examiner

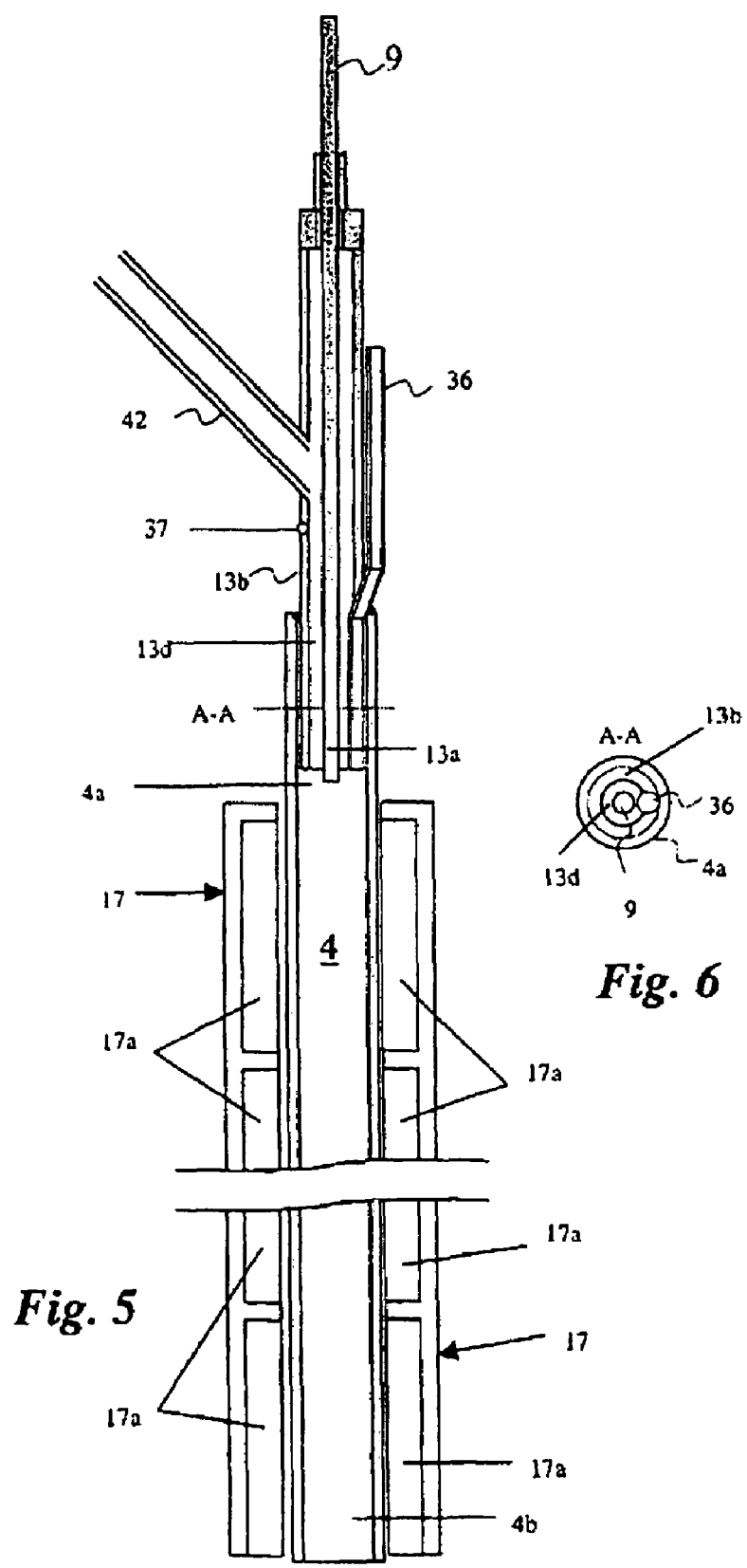

DOWNFLOW TEST UNIT FOR THE STUDY OF CATALYSTS IN SHORT CONTACT TIME REACTIONS BETWEEN THE CATALYST AND THE REAGENTS

RELATED APPLICATIONS

The present application is a Continuation of co-pending PCT Application No. PCT/ES02/00535, filed Nov. 15, 2002, which in turn, claims priority from Spanish Application Serial No. P 0102670, filed Nov. 20, 2001. Applicants claim the benefits of 35 U.S.C. §120 as to the PCT application and priority under 35 U.S.C. §119 as to said Spanish application, and the entire disclosures of both applications are incorporated herein by reference in their entireties.

SECTOR OF THE ART

The present invention refers to the technical field of laboratory test systems, particularly laboratory test systems applicable to the study of catalysts, and especially applicable to the study of catalysts in short contact time reactions between a catalyst and a reagent such as, for example, in the simulation of fluid catalytic cracking processes of hydrocarbons.

STATE OF THE ART

The FCC ("Fluid Catalytic Cracking") process is nowadays the heart of a modern refinery. The current tendency for improving the yield of FCC units is to work at an increasingly high reaction temperature and at contact times that are becoming shorter and shorter in order to increase the selectivity towards light olefins, the base chemical products in petrochemical processes. In order to maintain conversion levels, catalysts are added that can contain or be supported on mineral components such as zeolites. Such processes are known in themselves. So, U.S. Pat. No. 4,985,136 describes an ultra-short contact time FCC process in which the use is proposed of a catalyst with a zeolite content higher than 40% and a contact time in the interval of 0.1 to 2 seconds, preferably 0.2 to 0.5 seconds. This patent stresses the absence of a laboratory catalytic test for studying this process owing to the high activity of the catalyst used and the very short reaction time.

The usual types of laboratory test of conventional catalysts have some limitations. So, the test ASTM-D3907 for a fixed bed MAT (microactivity test) reactor or the fixed fluid bed (FFB) units are not well adapted to operations with very short contact times. They also function in a discontinuous way while the FCC process is a continuous process. The average conversion values that they provide on a test can be misleading when it comes to comparing catalysts with very different deactivation patterns. The fixed fluid bed offers better control over the reaction temperature and, according to the description of U.S. Pat. No. 6,069,012, it offers the possibility of being able to vary the contact time of the hydrocarbons with the catalyst without changing the catalyst/feed ratio of the feed rate. Nevertheless, this contact time is not well defined.

Pilot units simulate industrial plant data much more accurately, but they are expensive and consume large amounts of catalyst and feed in comparison with the needs of the present invention.

Some units have recently been developed for small-scale simulation of catalytic cracking in a much more realistic way than standard ASTM-D3907: Riser Simulator® (DeLasa U.S. Pat. No. 5,102,628) and Microriser® (Helmsing, Makkee, Moulijn, Chem. Eng. Sci., 51, pp. 3039-3044, 1996). In particular, the residence time of the gas in the reactor is controlled better and can become very short (0.15 seconds for the Microriser). Nevertheless, they still present some disadvantages. In the Riser Simulator, the contact time varies between 2 and 20 seconds, which is too long a time for simulating the new FCC processes that are proposed; also, the recovery of the heaviest part of the reaction products can be a problem. In the Microriser, the operation is isothermal, which means that the thermal shock between the hot catalyst and the colder load cannot be reproduced. Another drawback lies in the changes of direction undergone by the catalyst in the proposed design, namely, back-mixing could take place in the bends of the reactor. In order to minimise this effect, the catalyst has to be swept along at high speed (more than 4 meters a second), which implies that the quantity of inert necessary for ensuring piston flow of the catalyst lowers the partial pressure of the hydrocarbons to around ⅕ of the total pressure at the inlet of the feed, and high concentrations of catalyst cannot be used in the reactor. Furthermore, the quantities of solid used for a test are relatively high, around 500 grams, and the times needed for separation of the products and of the solid and sweeping of the absorbed products ("stripping") are greater than 10 minutes. This means that, for a process in which the contact time between the catalyst and the feed is less than one second, a stripping time of 10 minutes or more will be disproportionately long and can lead to additional cracking occurring in that stage producing undesired products such as $H_2$, methane and ethane.

The aim of this invention is a laboratory unit capable of simulating the continuous operation of the FCC, or other operations such as for example selective oxidations of hydrocarbons, carried out in a down transported flow reactor and which permits a study of the activity and selectivity of catalysts, and the influence of the load on the reactivity and selectivity of the catalyst. The residence times in the reactor are short, between 0.1 and 5 seconds, the unit can work in a wide range of catalyst/feed ratios, between 2 and 100, at high temperatures, between 100 and 750° C., and with short separation times between catalyst and reaction products, between 20 and 200 seconds, following the reaction phase. Moreover, the reaction system has the advantage that the total duration of the experiment is short, between 20 and 300 seconds, requiring small quantities of catalyst and feed (between 10 and 200 grams). The feed of solid being in the downwards direction, as occurs in the reactor of the present invention, has a series of advantages with respect to the classical configuration of a rising flow reactor (reactor riser). So, as the gas does not have to be pushed to the solid in order to advance through the reactor, there does not exist any minimum speed of gas required for it to circulate through the solid. Consequently, there are no limitations on the density of the solid as in the case of the classical riser type reactor, owing to the required minimum speed of gas. The reactor can be as short as is desired without prejudicing the general circulation of the solid in the plant, consequently, very short residence times of the catalyst and of the products in the reactor can be achieved. Finally, in a circulation in the downwards direction, much less back-mixing of the catalyst takes place and the flow is quite a bit more like piston flow. This permits the residence time, both of the gas and of the solid, to be controlled with much greater reliability.

DESCRIPTION OF THE INVENTION

In order to overcome the drawbacks inherent to the units and test methods of the state of the art, and to achieve the advantages described above, the present invention provides a test unit, particularly for the study of catalysts in short contact time reactions between at least one catalyst and at least one reagent, which comprises a reactor with at least one load inlet for introducing feed comprising at least one reagent and at least one catalyst which must intervene in the test reaction, at least one discharge outlet for discharge of the catalyst and of reaction products resulting from the test reaction, a separator in which the catalyst is separated from the reaction products, the reactor having an admission inlet through which the reaction products and the catalyst gain access to the separator, and at least one evacuation outlet for evacuating at least the reaction products separated from the catalyst, and means of heating for heating at least part of the unit. In this unit,

- the reactor is a down transported flow reactor with a height/diameter ratio of at least 5, particularly from 50 to 500, and can be a tubular reactor,
- the load inlet is arranged in an upper part of the reactor and the discharge outlet is in a lower part of the reactor,
- the admission inlet and at least one evacuation outlet are arranged in an upper part of the separator,
- the means of heating comprise at least a first preheater with at least one tank housing the catalyst prior to the test reaction for heating the catalyst to the desired temperature before it is loaded into the reactor (4), the first preheater having at least one outlet connected to the inlet of the reactor via a load duct in such a way that, between said outlet from the first preheater and said load inlet for the reactor, some obturator means are provided which are closed when the catalyst is being heated to the desired catalyst temperature in the first preheater and they open when the catalyst has become heated to the desired catalyst temperature for discharging the catalyst into the reactor,
- the separator is internally divided by a porous element, preferably a porous plate manufactured, for example, from quartz or stainless steel, and preferably of INCONEL 600, into an upper chamber and a lower chamber, the porous element being permeable to gas and impermeable to solid particles of catalyst, said admission inlet being linked with the upper chamber, and
- the discharge outlet from the reactor links with said admission inlet.

In view of the fact that, according to the invention, the test unit is based on a down flow of the feed, it will also be identified as "microdowner" or by the abbreviation "MD" in the present descriptive specification.

In a preferred embodiment, the first preheater comprises a plurality of tanks each intended to house and heat separate catalysts intended for a plurality of tests. In this embodiment, the tanks can be connected with said load inlet to the reactor via the load duct, with individual obturator means being inserted between each tank and said load inlet, or each of the tanks can be connected to said load inlet to the reactor via an individual load duct, in which case each individual load duct has individual obturator means inserted in it. The presence of several tanks in the first preheater permits the successive testing of several catalysts continually, without any need for handling by the operator.

The obturator means can be arranged in such a way that, when closed, they isolate the first preheater from the reactor. So, the obturator means can, for example, be commercial HT (High Temperature) valves among which can be found valves that operate up to a temperature of 816° C. In a preferred configuration, each tank has a lower narrow and lengthened part with a height/diameter ratio of between 5 and 50, in order to thereby achieve a more uniform temperature in the entire tank. The tank has a sufficient volume for containing the amount of catalyst needed for conducting a test, plus an additional quantity of 10 to 30 g of catalyst which serves to maintain a seal between the reactor and the atmosphere in the tank.

Preferably, the first preheater has sufficient heating capacity for heating up the catalyst to a temperature between 100° C. and the maximum temperature that the obturator means can resist and maintaining their functionality to function, in other words, a maximum temperature of around 800° C. when the obturator means are commercial HT valves. Also, the first preheater can be provided with a pressurisation gas inlet for filling each tank with pressurisation gas which creates an internal pressure that drives the catalyst towards the reactor when the obturator means are opened. The outlet from the first preheater is preferably also connected to a first gas line which conducts fluidisation gas which fluidises the catalyst before they are loaded into the reactor.

In an embodiment of the reactor, the load inlet for the reactor comprises a reagent inlet which links with a reagent load line, and a catalyst inlet, linked to the catalyst load duct. In this embodiment, the load line can be connected via a first end to a load injector for injecting reagents through the reagent inlet of the reactor, the load injector also being able to be connected to a supply line that conducts an inert gas which is mixed with the reagents before they are loaded into the reactor. In this case, the injection of the reagents to the reactor can be done via a first tube of small diameter (for example, $1/16''$), while the inert gas can be introduced into the reactor by means of a second tube of somewhat larger diameter than the first tube (for example, $1/8''$) which surrounds the first tube, in other words, the first tube and the second tube are concentric in such a way that the inert gas passes through the space between the internal wall of the second tube and the external wall of the first tube, destroying the drops of liquid exiting from the first tube. This configuration has the advantage of improving the quality of atomisation of the reagents by means of minimising the drops formed by the reagents, and the reagents are prevented from becoming deposited and adhered to the internal wall of the reactor in the reagent inlet zone. The space between the first and second tube is preferably narrow in order to obtain a high rate of input of the gas which provokes greater breakage of the drops of reagents entering the reactor and increasing their rate of vaporisation. In this way, the injected reagents and the inert gas travel together in the reactor in the downwards direction.

At least one directing valve can be inserted into the load line, which valve, in a first position, permits the flow of reagents to the reactor and in a second position prevents the inlet of the flow of reagents to the reactor. This directing valve can be a three-way valve with low dead volume which, in addition to those two positions, can also adopt a third position in which the reagents are directed towards, for example, an external receptacle.

In a section of the load line, a second preheater can be provided for heating the reagents before they are loaded into the reactor and, preferably, it is also heated at least between the second preheater and the inlet to the reactor or, when this is available, until the inlet of the injector. The second preheater preferably has sufficient heating capacity for heating the reagents to a reaction temperature between 100 and 400° C. Nevertheless, the temperature to which the reagents, which simulate a large part of FCC processes, are heated lies between 120 and 300° C. Moreover, in a second end of the load line, in other words, the end far away from the first end, the load line can be connected to a feed pump which pumps the reagents towards the reactor.

The reactor can furthermore be provided with a heating system with sufficient heating capacity for maintaining a reaction temperature of between 100 and 700° C. in the reactor. The heating system can comprise sector heating elements with heating capacities that can be adjusted by sectors, in order to maintain the reaction temperature. To achieve this, the heating system can be adjusted in such a way that the reaction temperature is reached and maintained in accordance with temperature measurements made by at least one temperature sensor selected from the group consisting of a first temperature sensor which measures a first temperature in an upper part of the reactor, which can be, for example, a thermocouple provided in a zone close to the load inlet of the reactor, a second temperature sensor which measures a second temperature in a lower part of the reactor, and a third temperature sensor which measures a third temperature in an intermediate part between said upper part and said lower part.

Conveniently, the temperature sensor elements can be linked with a programmable temperature control unit, to which the sensor elements inform of the temperatures measured, in such a way that the temperature control unit governs the heating means as a function of the measured temperatures and the programmed temperatures with respect to each test conducted.

By means of this arrangement, the temperatures in the zones of the reactor can be adjusted to the desired temperatures.

The separator preferably has an upper diameter greater than the diameter of the reactor, usually 2 to 100 and preferably 5 to 15 times greater than the diameter of the reactor. Furthermore, the upper chamber of the separator preferably has a height/diameter ratio of 0.2 to 10, habitually 0.3 to 0.5, above the porous element. The lower chamber of the separator in turn, preferably presents a gas access connected to a second gas line which conducts pressurised gas which is usually an inert venting gas. In an embodiment of the invention, the access gas is also connected to a third gas line which conducts an oxidising gas. The functions of these gases will be described further below in this specification. In addition, the separator can be provided with at least one heating element with sufficient heating capacity for maintaining the chambers of the separator at a temperature between 100 and 600° C. A usual temperature in the simulation of an FCC reaction is from 400 to 550° C., although the temperature in the separator can be adjusted to a relatively lower temperature than the reaction temperature, for example, to a temperature between 400 and 500° C., in such a way that the reaction products undergo a certain cooling when they leave the reactor and enter the separator, which reduces the rate of undesired catalytic and thermal reactions in the separator. In order to detect the temperature in the separator, the unit can be fitted with a fifth temperature sensor which is preferably provided just above the porous plate.

In the separator, the catalyst is separated from the gas by inertia. So, while the catalyst collides with the porous element and its particles are distributed on the surface of the porous element, the gases that are present expand in the separator and can be extracted through the evacuation outlet which is conveniently fitted with a filter that retains the particles of the catalyst which might have been suspended in the gas, in order to prevent those particles from being extracted along with the gases. In this way, the catalyst becomes retained in the upper chamber of the separator.

When the separator has the gas access connected to the gas line described above, the reaction products that are adsorbed or absorbed in the catalyst, and which have therefore not been extracted via the evacuation outlet along with the gas, can be desorbed from the catalyst retained on the porous element by means of a sweeping process consisting of fluidisation of the catalyst through the introduction of a fluidisation gas via the gas access, in such a way that the gas enters the lower chamber, before crossing the porous element in such a way that the volume of the lower chamber acts as a preheating section for the fluidisation and separation gas. The rate of flow of the gas via the porous element must be sufficiently high for fluidising the catalyst uniformly and it can be the same gas as that used during the reaction or it can be another gas. The desorption of the reaction products from the catalyst can be accelerated by means of applying vacuum pulses which help to clean the catalyst. In this way, the reaction products which have been desorbed from the catalyst are also extracted via the evacuation outlet of the separator.

Preferably, the evacuation outlet from the separator is suitable for being connected to a collection system for liquid and gaseous products which are evacuated from the separator. This system preferably includes a distribution valve which, during the separation phase, in other words when the reaction products are evacuated from the separator while the catalyst remains retained in the porous element, and during the "stripping" phase of the retained catalyst, in other words, during the desorption of the reaction products adsorbed or absorbed in the retained catalyst, sends the reaction products and the corresponding fluidisation gas via a first outlet line to an analysis system for the reaction products, while, during the regeneration phase of the catalyst, it sends the gases generated in the regeneration via a second outlet line which conducts those gases to, for example, the oven mentioned earlier where they are oxidised for their later analysis.

The analysis system for the reaction products can include means of collection that are conventional in themselves, such as for example one or several traps maintained at a constant controlled temperature lying between −50° C. and 50° C. for liquid reaction products, and one or several water receptacles for the gases, or by other means in which the volume is controlled by sensors of, for example, the optical, capacitative or inductive type, or by weighing of the water displaced in a burette. The analysis of the gaseous products collected can be done, for example, in a gas chromatograph.

When the gas access of the separator is also linked to the third gas line, in other words, to the oxidising gas line, a regeneration of the catalyst can be done in the same separator. In this case, the oxidising gas, such as for example air, is introduced through the gas access, and the gases that are produced in the generation are also extracted via the evacuation outlet from the separator. These gases can then be led to an oven containing an oxidation catalyst which catalyses the complete oxidation of CO present in those gases to $CO_2$, in such a way that the $CO_2$ and the water contained in the resulting combustion gases can be analysed by means of the appropriate analysis technique, conventional in themselves, such as IR—gas chromatography, mass spectroscopy or any other adequate conventional method.

Independently of whether it has been regenerated or not, the catalyst can be extracted from the separator in order to collect it in, for example, a collection tank, without having to wait for the catalyst to cool. The extraction of the catalyst is preferably done by means of a powerful current of gas with sufficient strength to sweep the particles of catalyst through an extraction outlet present in the upper chamber of the separator and connected to an extraction line, fitted with a depressurisation valve which opens after separation of the reaction products in order to permit extraction of the catalyst. Alternatively, or complementary to this, the extraction of the catalyst can be done by pressurising the separator by means of introducing the gas and then suddenly opening the depressurisation valve, in such a way that the separator undergoes rapid depressurisation through the second extraction outlet, and the gas sweeps the particles via that extraction line towards the collection tank.

The test unit of this present invention can conveniently also include a programmable gas flow control system which, on the basis of gas pressure values detected by gas pressure measuring means, governs gas regulation means inserted in at least one gas conduction line, in order to supply under controlled conditions at least one inert gas to the first preheater, to the reactor and/or to the separator. The gas pressure measuring means can include at least one pressure meter selected from the group consisting of:

a first pressure meter for measuring first pressures in the first preheater, a second pressure meter for measuring a pressure difference between a first point in the second gas line conducting pressurisation gas and which connects the first heater and a gas access in the lower part of the separator, a third pressure meter for measuring second pressures in the admission inlet to the separator, and a fourth pressure meter for measuring third pressures existing between the second point in the second gas line and the gas inlet for the separator, while the gas regulation means comprise at least one regulator means selected from the group consisting of:

a first regulator means provided between said first point and said second point in the second gas line, a second regulator means which links the first preheater with the atmosphere, a third regulator means provided in the first gas line which can be, for example, a non-return valve, a fourth regulator means provided between the second point in the second gas line and the gas inlet to the separator, and a fifth regulator means connected to an evacuation outlet from the separator.

The pressure meters and the pressure regulating means are conveniently connected to the flow control system for gases in such a way that the system can detect differences between pre-established values and the measured pressure values, and order the regulating means to act so as to correct the discrepancies between those values.

According to the invention, the fluidisation gas used must not interfere neither with the catalyst nor with the reagents nor with the reaction products, because of which it is preferred if the gas is an inert gas such as nitrogen or a noble gas such as argon, neon or helium.

The tank or tanks of the first preheater, the reactor and the separator are preferably made of stainless steel, though they can also be of other heat-resistant materials which do not undergo any changes in their physical or chemical properties in the temperature ranges to which the test reactions conducted in the unit are subjected.

In order to vary the conversion, the flow of feed, for example, is fixed and the flow of catalyst is varied, thereby varying the ratio of catalyst to feed without appreciably modifying the residence times of the gas and of the catalyst in the reactor. If necessary, another value can be chosen for the flow of feed in order to achieve a different interval of conversions. The duration of the test will be that appropriate for having sufficient reaction products for being analysed. The limits for the duration of the test (operation times) are fixed according to the following two recommendations: the lower limit is indicated by the need for the transition period at the beginning of the test to be sufficiently short with respect to the total duration of the test, so as not to have any appreciable effect on the results. For this particular unit it is recommended that the reaction time should be no less than 20 seconds; the upper limit is fixed according to the amount by which it is wished to reduce according to the dimensions of the collection sections for the catalyst and reaction products such as for example the volume of gases collected, quantity of catalyst or feeds used.

The residence time of the gas in the reactor varies by modifying the flow of feed. The residence time of the solid depends on the residence time of the gas, and in the event that the speed of the gas is not significantly higher than the terminal speed of fall of the catalyst then the residence time of the catalyst and that of the gas have to be distinguished. The residence time of the gas is calculated on the basis of the volume of the reactor, the temperature and pressure in the reactor, the flow of feed, the average molecular weight of it and the distribution of products at the outlet.

For each test, the temperature is adjusted in such a way that the temperature of the physical mixture and of the feed is always the same in a series of tests that it is wished to compare, independently of the ratio of catalyst to feed (CTO) chosen for each test. Nevertheless, this is not a limitation since the temperature of the physical mixture and the preheating of the catalyst can always be controlled for the CTO ratio that has been set.

BRIEF DESCRIPTION OF THE FIGURES

The invention will now be described on the basis of certain drawings wherein

FIG. 5 is a schematic view in longitudinal cross-section of the reactor shown in FIGS. 1, 3 and 4, and FIG. 6 is a view of the reactor shown in FIG. 5 in transverse cross-section through the line A-A.

Figure 1:
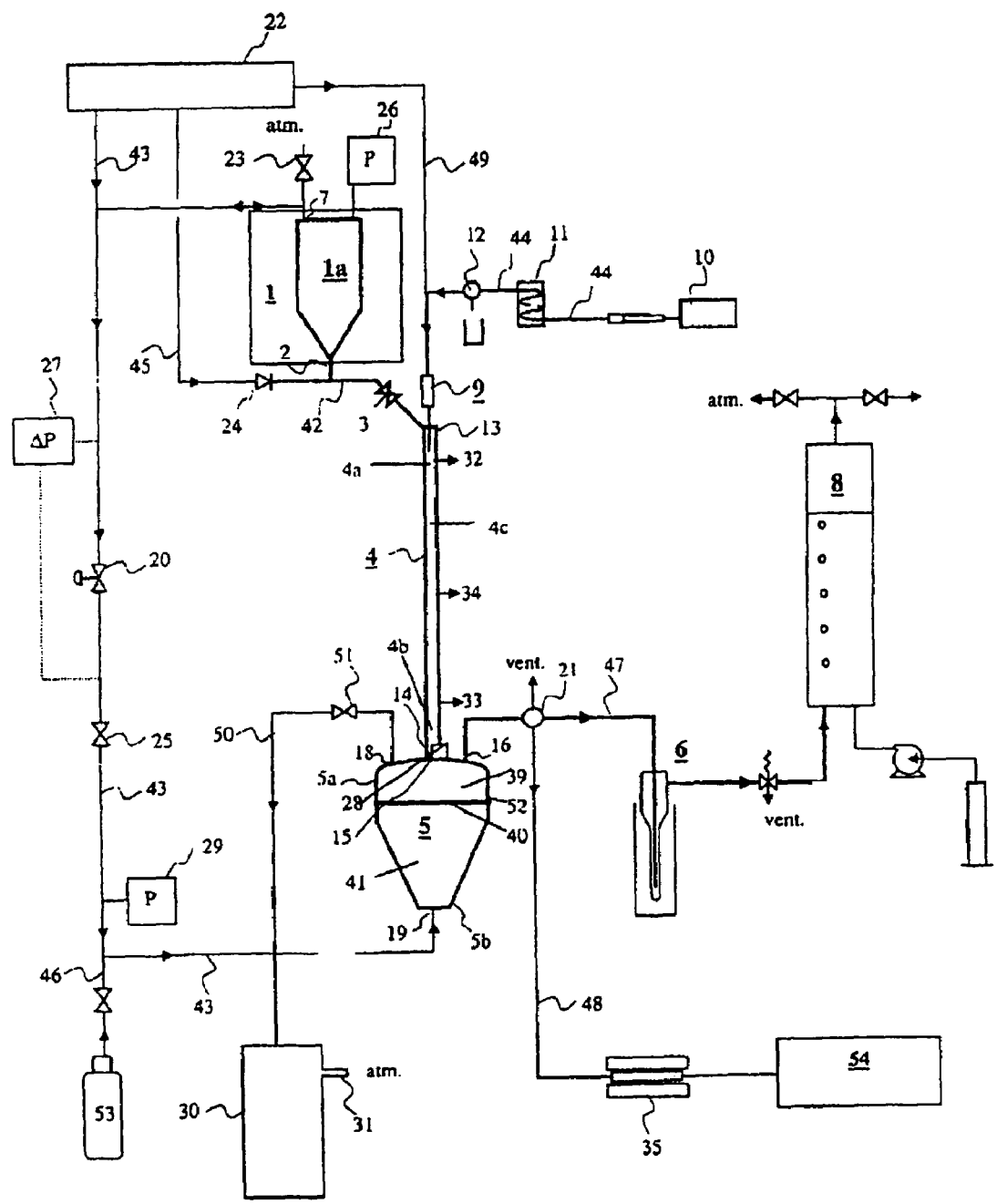
FIG. 1 is a diagram of the general functioning of a test unit according to an embodiment of the invention.

These figures include numerical references defining the elements listed below.

1 first preheater
1*a* tank for the catalyst in the first preheater
2 outlet from the first preheater with a single tank 1*a*
2*a* outlet from the first preheater with several tanks 1*a*

3 obturator means (HT valve)
3a individual obturator means
4 reactor (tubular)
4a upper part of the reactor
4b lower part of the reactor
4c intermediate part of the reactor
5 separator
5a upper part of the separator
5b lower part of the separator
6 trap for collection of liquids generated during reaction and liquids exiting from the separator
7 pressurisation inlet for pressurisation gas to the preheater 1
8 receptacle collecting the gas generated during the reaction and exiting from the separator
9 load injector with which the reagent is injected into the reactor
10 feed pump for the reactor
11 second preheater (for the feed)
12 directing valve (12) for the feed (e.g., three-way valve which changes the feed to the reactor when the reaction starts)
13 inlet to the reactor
13a load inlet to the reactor for reagent
13b load inlet to the reactor for the catalyst
13c addition of inert gas for mixing with the load
13d annular space
14 discharge outlet from the reactor
15 admission inlet for the separator
16 evacuation outlet of the separator for the products (in vapour form)
17 heating system for the reactor
17a sector heating elements for the heating system
18 evacuation outlet for the catalyst
19 gas access to the separator
20 first pressure regulating means (valve in line 43 through which the fluidisation gases of the solid and pressurisation gases pass, the valve originates a loss of load which permits the solid flow to be regulated)
21 distribution valve in the outlet of products from the separator (line 47) which diverts the gases produced during the regeneration phase to line 48
22 gas flow control system
23 second pressure regulating means (escape valve to the atmosphere)
24 third pressure regulating means (non-return valve)
25 fourth pressure regulating means (stop valve for line 43 when the catalyst is regenerated)
26 first pressure meter
27 second pressure meter
28 third pressure meter
29 fourth pressure meter
30 tank for collection of the catalyst after the test, coming from the separator through line 50
31 gas outlet from tank 30
32 first temperature sensor
33 second temperature sensor
34 third temperature sensor
35 oven containing a combustion catalyst permitting complete oxidation of CO to $CO_2$
36 inlet for thermocouples for measuring the temperature inside the reactor at different heights
37 side inlet for a thermocouple intended to check the arrival temperature of the catalyst at the reactor
38 filter in the gas outlet from the separator
39 upper chamber of the separator
40 porous element (porous plate in the separator, against which the catalyst coming from the reactor runs up, separating the gases and catalyst by inertia)
41 lower chamber of the separator
42 load ducts connecting the outlet 2 from tank 1a with the reactor 4
42a individual load ducts connecting each of the tanks 1a with the reactor 4
43 second gas line (fluidisation gas line for fluidising the catalyst retained on the porous plate 40, it connects the store 1 with the lower part of the separator 5a and houses the valve 20)
44 reagents load line for carrying the reagents to the reactor
45 first gas line (line for addition of gas for aerating the catalyst in the store 1)
46 third gas line (line for addition of air or other oxidising gas which is introduced into the separator for regeneration of the catalyst)
47 first outlet line collecting the reaction products
48 second outlet line towards the analysis of regeneration gases from the catalyst
49 supply line for addition of an inert gas to the reagent
50 line for extraction of the catalyst from the separator after the test, for carrying it to the collection tank
51 fifth regulating means (depressurisation valve which opens after the test in order to rapidly depressurise the separator so that the catalyst can be swept along the line 50 to the tank 30)
52 fourth temperature sensor
53 source of oxidising gas
54 analysis system of combustion gases

DESCRIPTION OF EMBODIMENTS OF THE INVENTION

According to what can be seen in FIG. 1, the first preheater 1 includes a tank 1a wherein a catalyst is heated up prior to carrying out the test reaction. The outlet 2 from the preheater is connected with the load inlet 13 in the upper part 4a of the reactor 4, through a load duct 42 in which an HT valve 3 is inserted. The load duct 42 is connected through its other end to a first fluidisation gas line 45, which receives an inert fluidisation gas from a flow control system 22. Inserted in the first gas line 45 there is a non-return valve 24 which prevents back-flow of the fluidisation gas towards the control system 22.

Provided in the upper part of the tank 1 there is a first pressure meter 26 and a pressurisation inlet 7 for the inlet of an inert pressurisation gas, connected to a second gas line 43 which in turn also receives the inert gas from the gas flow control system 22.

Also connected to the load inlet 13 of the reactor 4 is a load injector which, on the one hand, is connected to a reagent load line 44 and to a supply line 49 for the addition of an inert gas, also connected to the control system 22, which inert gas is intended to disperse the reagents as they enter the reactor 4. The load line 44 has a section wherein a second preheater 11 is provided, intended for heating the reagents to the predetermined temperature before they enter the reactor 4 and, moreover, a directing valve 12 which, when it is open, permits the flow of reagents towards the injector 9. The reagents flow through the load line 44 driven by a pump 10.

The reactor 4 is provided with three temperature sensors, namely, a first sensor 32 in its upper part 4a, a second sensor 33 in its lower part 4b, and a third sensor 34 in its intermediate part 4c. In the lower part 4b of the reactor is the discharge outlet 14 for the reactor, linked to the admission inlet 15 in the upper part 5a of the separator 5.

The separator 5 is internally divided by a porous plate 40 into an upper chamber 39 which is accessed through the admission inlet, and a lower chamber 41 which communicates with a gas access 19 in the lower part 5b of the separator 5. Provided just above the porous plate 40 is a fourth temperature sensor 52. In the upper part 5a of the separator 5, a first evacuation outlet 16 for the reaction products and a second evacuation outlet 18 for the extraction of the catalyst are also provided.

The gas access 19 is also connected to the gas flow control system 22 via the second gas line 43. Moreover, the gas access 19 is connected to a source of oxidising gas 53 through a third gas line 46 wherein a valve is inserted. Furthermore, the second evacuation outlet 18 is connected to a collection tank 30 for the catalyst which has a gas outlet 31 conveniently provided with a filter (not shown in the figure), through an extraction line 50 wherein a depressurisation valve 51 is inserted.

The first evacuation outlet 16 is connected, through a distribution valve 21, to the analysis systems for the reaction products and for the products generated in the regeneration of the catalyst. The distribution valve 21 is connected to a first outlet line 47 which leads the reaction products extracted from the separator 5 to the analysis system comprising a trap 6 for the collection of liquid reaction products and a receptacle 8 for the collection of gaseous reaction products, which can in turn be connected to means of analysis of the reaction products, conventional in themselves. Moreover, the distribution valve 21 is also connected to a second outlet line 48 which leads the gaseous products generated in the regeneration of the catalysts to an oven 35 containing a combustion catalyst which permits complete oxidation of CO, present in the regeneration gases, into $CO_2$, with combustion gases being generated that are led to a combustion gas analysis system 54 wherein the $CO_2$ and water content of the combustion gases are analysed.

FIG. 1 also shows the pressure meter means 26, 27, 28, 29 which include the first pressure meter 26 for measuring first pressures in the tank 1a of the first preheater 1, the second pressure meter 27 for measuring a pressure difference between a first point in the second gas line 43 conducting the fluidisation gas and which connects the first heater 1 and the gas access 19 in the lower part 5b of the separator 5, the third pressure meter 28 for measuring second pressures in the admission inlet 15 to the separator 5, and the fourth pressure meter 29 for measuring third pressures existing between the second point in the second gas line 43 and the gas access 19 for the separator 5.

In turn, FIG. 1 also illustrates the arrangement of the gas regulation means 20, 23, 24, 25, 51 comprising the first regulator means 20 provided between said first point and said second point in the second gas line 43, the second regulator means 23 which links the first preheater 1 with the atmosphere, the third regulator means 24 provided in the first gas line 45, the fourth regulator means 25 provided between the second point in the second gas line 43 and the gas inlet 19 to the separator 5, and the fifth regulator means 51 connected to an evacuation outlet 18 from the separator 5.

It can also be seen in FIG. 1 that the upper part 5a of the separator 5 has a transverse section approximately ten times greater than that of the reactor 4.

Figure 2:
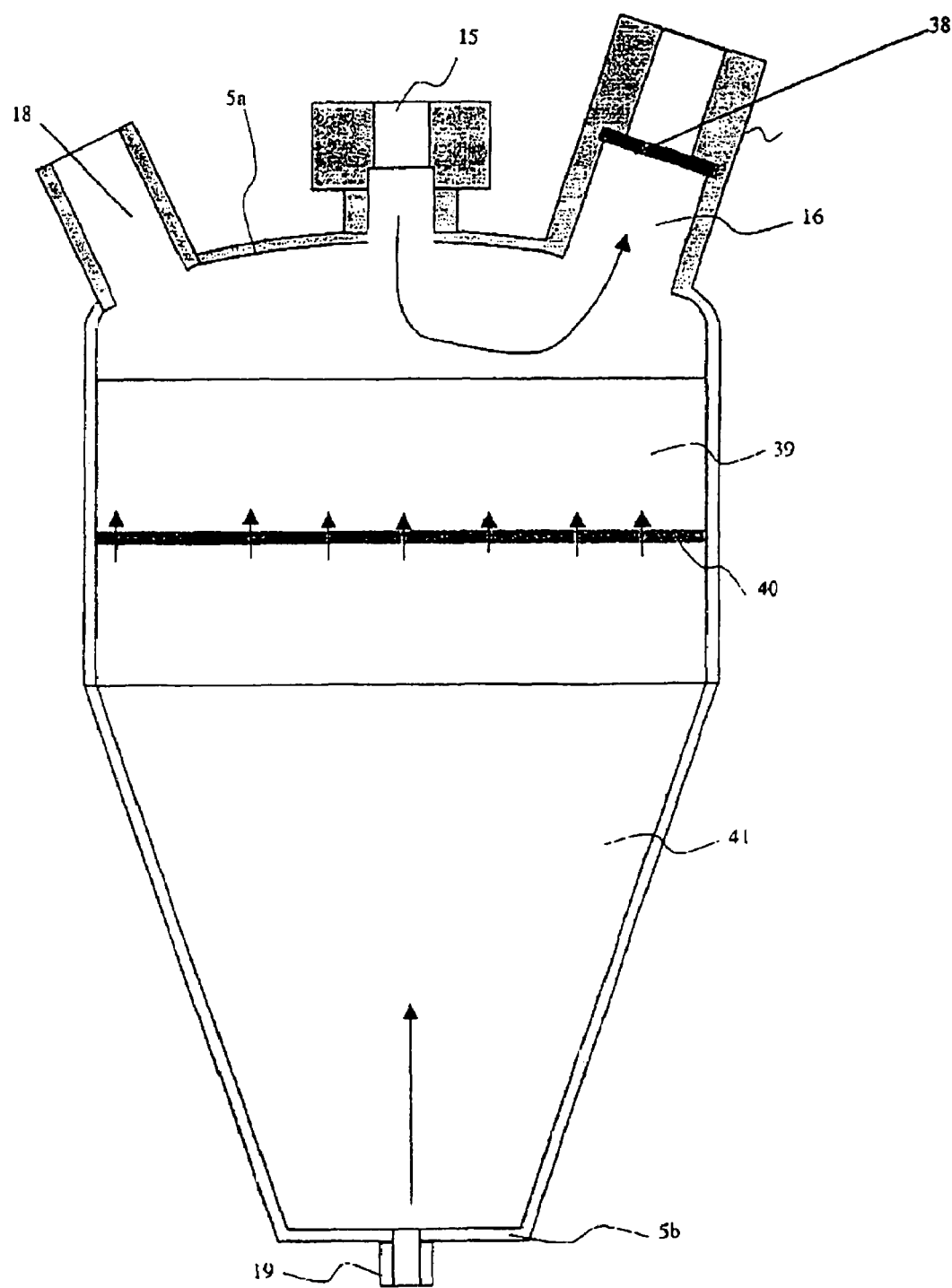
FIG. 2 is an elevation view in cross-section of an embodiment of the separator.

In FIG. 2 the general characteristics of the separator 5 can be seen. So, in the upper part 5a of the separator 5 the admission inlet 15 can be found, the evacuation outlet 16 for extraction of the reaction products and the regeneration products of the catalyst, along with the second evacuation outlet 18 for extraction of the catalyst, while in the lower part 5b of the separator 5 the gas access 19 is located. The interior of the separator 5 is divided by a porous plate 40 into an upper chamber 39 and a lower chamber 41. The lower chamber 41 in turn has its lower part with an inverted tronco-conical configuration, which favours the distribution of heat inside the separator 5. Moreover, it can also be seen that the upper chamber 39 of the separator 5 has, above the porous plate 40, a height/diameter ratio of 0.3 to 0.5.

Figure 3:
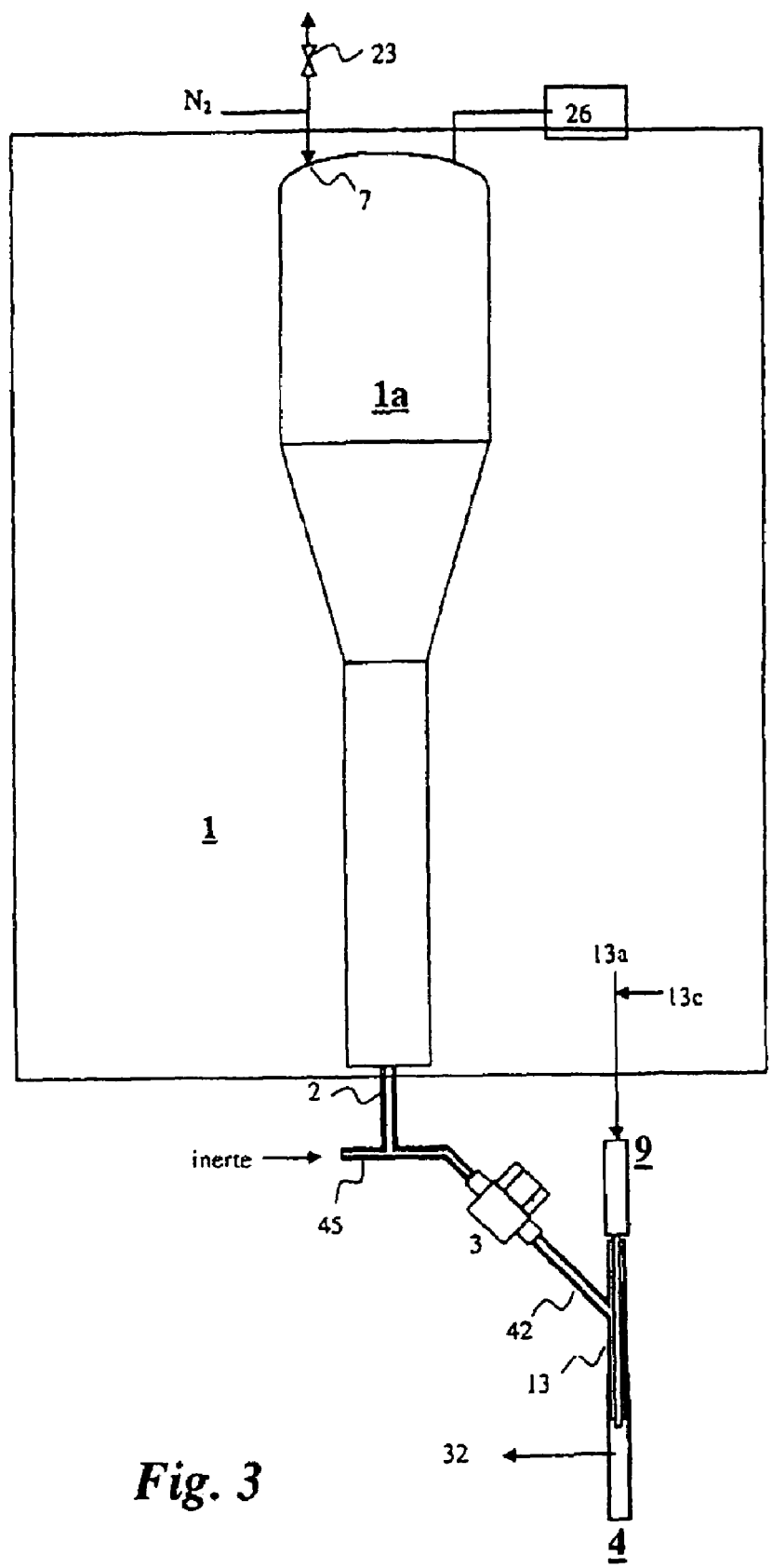
FIG. 3 is a partial schematic view of an embodiment of the invention with a single preheater and schematically showing the preheater and the reactor, along with the connection between the reactor and first preheater.

FIG. 3 shows with somewhat more detail the communication between the tank 1a and the reactor 4. So, it can be seen that the outlet 2 from the tanks 1a receives fluidisation gas, nitrogen, from the duct 45 so that said gas sweeps the catalyst towards the reactor 4 through the load duct 42 wherein the HT valve 3 is inserted.

Figure 4:
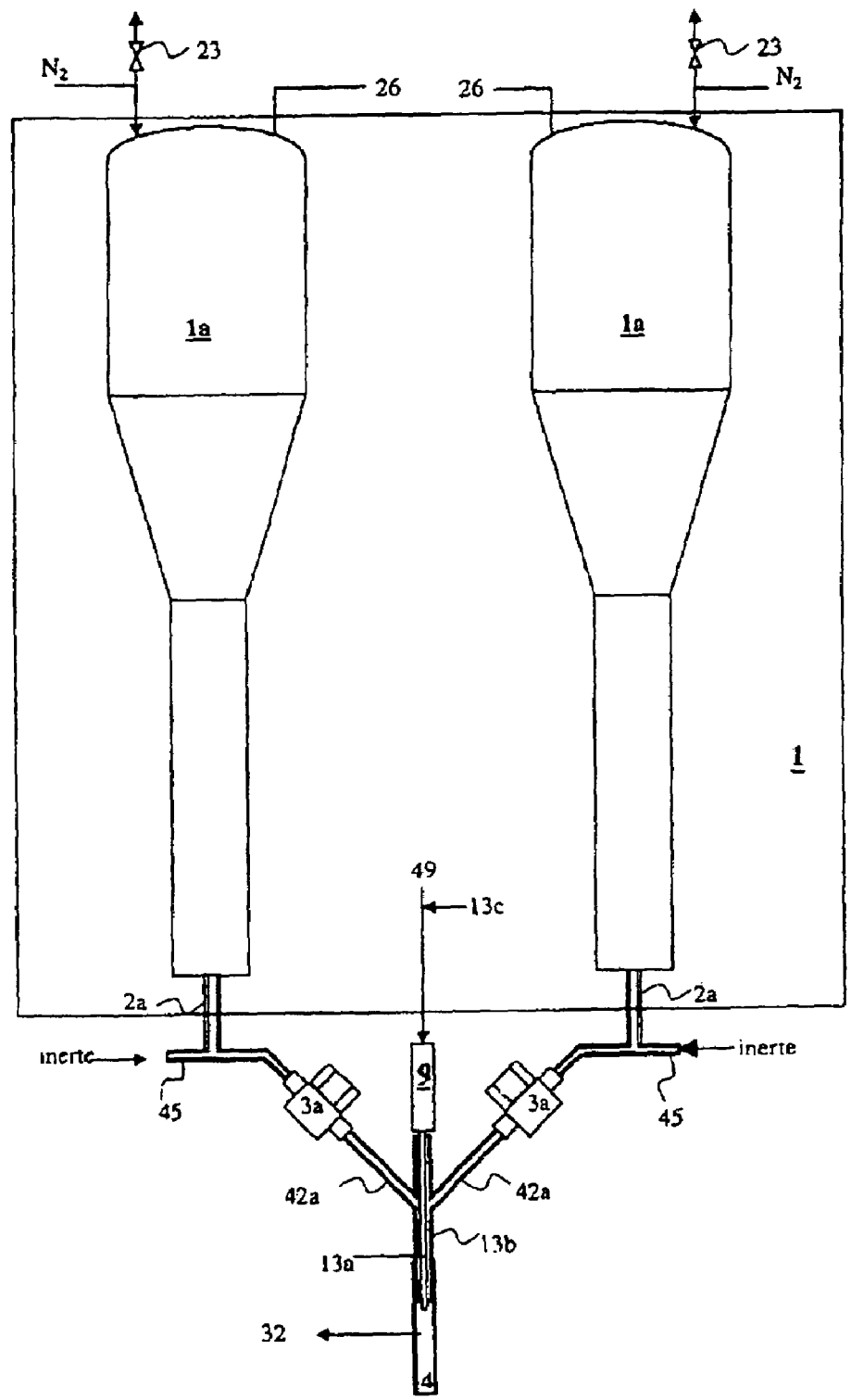
FIG. 4 is a partial schematic view of another embodiment of the invention with two first preheaters and schematically showing the preheaters and the reactor, along with the connection between the reactor and said first preheaters.

FIG. 4 shows an embodiment in which the first preheater 1 comprises two tanks 1a, the outlets 2a of which are connected to individual load ducts 42a in each of which an individual HT valve 3a is inserted. Both load ducts 3a lead to a load inlet 13b for the catalyst, in the upper part 4a of the reactor 4. Although FIG. 4 shows an embodiment wherein the preheater only has two tanks 1a, their arrangement and connection to the reactor 4 can be designed in an analogous manner for a first preheater 1 with a greater number of tanks 1a, arranged in a row or circularly.

FIGS. 5 and 6 show in greater detail an embodiment of the inlet 13b of the load duct 42 of the injector 9, the load inlet 13a for the reagents and an inlet 36 for thermocouples in the upper part 4a of the reactor 4, along with the heating system 17 with sector heating elements 17a. It can be observed that in the embodiment shown in these figures, the load inlet 13a comprises a central tube surrounded by a concentric outer tube 13b corresponding to the load inlet 13b for the catalyst, in such a way that between the outside wall of the central tube and the inside wall of the outer tube there is an axial annular space 13d defined via which the catalyst enters swept along by the corresponding inert fluidisation gas. The internal diameter of the outer tube is adjusted so that the annular space 13d formed between the two tubes is very narrow, with the aim of obtaining a high speed of gas and a greater effect of breaking up the drops of liquid that are injected. In this way, the inert gas and the catalyst form an annular "curtain" around the outlet mouth of the central tube corresponding to the load inlet 13a for the reagents, in such a way that the small drops of reagent that are injected are prevented from adhering to the inner wall of the upper parts 4a of the reactor 4, at the same timer as achieving an intimate mix of reagents with the catalyst.

Furthermore, it can also be seen that the inlet 36 for thermocouples consists of a duct permitting access to the interior of the reactor 4. The thermocouples are, for example, the first, second and third temperature sensor 32, 33, 34 described earlier in relation to FIG. 1.

Reactor 4 is surrounded by a heating system 17 which, in the embodiment shown in FIG. 5, comprises sector heating elements 17a whose heating capacity can be individually regulated in line with the deviation of the temperatures measured by the temperature sensors 32, 33, 34 shown in FIG. 1, from the predetermined reaction temperature for each test reaction that is carried out.

According to what is revealed from the foregoing description of FIGS. 1 to 6, the test unit or microdowner MD unit consists of a first preheater 1 which houses one or several tanks for the preheating of the catalysts, connected via their outlets 2, 2a to the same reactor 4. Unlike in any other conventional system of the riser type, this permits the testing of several catalysts continually without any handling by the operator. That connection also permits the flow of solid being fed to the reactor to be regulated, for example with a system of one or more openings 2, 2a and valves 3, 3a. The catalyst is preheated to a temperature between 100° C. and the maximum temperature that the HT valve 3 can resist. Nowadays, there exist commercial valves operating up to 81620 C.

The catalyst can be fluidising during the preheating. The fluidisation gas is added by line 45 and flows upwards to the catalyst tank.

The feed of the reagent is done by means of the pump 10, which, as with the gas flow control system 22 and the means of heating 1, 11, 17, 17a is preferably controlled by a central unit wherein the conditions of time, temperature, pressure, etc., are programmed for each test it is wished to conduct. The three-way valve 12 with low dead volume controlled by the control system 22 changes the feed towards the reactor when the reaction starts, while the second preheater 11 raises the temperature of the feed to the desired temperature prior to injecting it into the reactor 4. The reagent load line 44 is preferably heated from the second preheater 11 until the injector 9.

The pressure is measured in the tank 1a and at the admission inlet 15 for the separator 5. This latter pressure is basically the same as in the reactor since the load pressure in the separator 5 is very low. So, the loss of load along the reactor 4 is generally less than 1 mbar. The pressures can be recorded by the central unit. During the test, the feed can be mixed with an inert added by the supply line 49.

The MD reactor 4 is tubular, of constant cross-section though it can also have variable cross-section, with an L/D ratio of 5 or more, preferably between 50 and 500. This reactor 4 connects directly with the separator 5. The catalyst and the vaporised products travel together in the reactor 4 in the downwards direction. The temperature of the reactor can vary between 100 and 750° C. The temperature is preferably measured in the reactor 4 at least at the three points mentioned above, namely in the upper part 4a, in the intermediate part 4c and in the lower part 4b.

The central unit (not shown in the drawings) stores the evolution of the temperature during the course of the test with a frequency of, preferably, at least one set of data every 2 seconds.

The role of the separator 5 is to provide the shortest possible separation and stripping operation, between 20 and 200 seconds. This reduces additional reactions in the separator 5, mainly producing hydrogen, methane and ethane. The separation temperature can be between 100 and 600° C., preferably the usual temperature for an FCC simulation which is normally between 400 and 550° C. In the simulation of the FCC reaction a temperature between 400 and 500° C. can be preferred, so that the reaction products and the solid undergo a certain cooling at the outlet from the reactor 4. In this way the speed of the catalytic reactions, and also of undesired thermal reactions that can take place in the separator 5, is reduced. The catalyst is separated from the gas by inertia: while the catalyst collides with the surface of the porous plate 40 and is thereby uniformly distributed on the surface of the plate 40, the gases expand in the separator 5 and exit through a filter 38 which retains the particles of catalyst which might have been suspended in the gases. The catalyst is fluidised on the plate 40 by means of gas from the line 43. The speed of the gas through the plate 40 must be sufficient for uniformly fluidising the catalyst. The flow of gas via the plate 40 during the separation stage can be the same as that used during the reaction or it can be conveniently varied. The temperature of the catalyst is measured by means of the temperature sensor 52 provided just above the plate 40. The volume below the plate 40, in other words, the lower chamber 41 of the separator 5, acts as a preheating section for the separation and stripping gas. The desorption of products can be accelerated by means of vacuum pulses which help to clean the catalyst.

The reactor 4, the separator 5 and the catalyst tank 5 can be made of any material that can withstand temperatures of up to 800° C., though stainless steel is preferred. The porous plate can be made of quartz or stainless steel, preferably INCONEL 600 on account of its mechanical strength and resistance to temperature.

The evacuation outlet 16 from the separator 5 is connected to a collection system for the products in liquid and gaseous form. The liquids generated during the reaction phase and the stripping phase are collected in one or more traps 6, at a constant controlled temperature lying between 50 and −50° C. The gases are collected in the receptacle 8 by displacement of water or by any other means wherein the volume is controlled by sensors of any type, such as for example: the optical, capacitative or inductive type, or by weighing of water displaced from the burette. The analysis of the reaction gases is done by displacement from the receptacle 8, and the gas are analysed in a gas chromatograph or any other system of analysis.

The regeneration of the catalyst can be carried out in the same separator 5 or in a separate system to which it is transferred by pneumatic means. When the regeneration is done in the same separator 5, air or any other oxidising gas is introduced through the line 46. The valve 21 changes the outlet path of the line 47 (collection of reaction products) towards line 48 (analysis of the regeneration gases). Alternatively, the catalyst can be collected without regenerating and determining the coke on the catalyst by means of a specific apparatus.

The combustion gases pass through an oven 35 with a catalyst that permits complete oxidation of CO to $CO_2$. The $CO_2$ and the $H_2O$ from the combustion gases are analysed by means of suitable techniques such as IR, gas chromatography, mass spectrometry or any other known procedure.

Once the test is ended, the catalyst is withdrawn from the unit and collected in the tank 30, without any need to wait for cooling of the separator. The transfer consists of sweeping the catalyst from the separator 5 with a powerful current of gas produced, by example, by the sudden depressurisation of the separator through the line 50.

In a preferred configuration, each catalyst tank la has two parts: the lower part is narrow and long, with a length/diameter ratio of between 5 and 50, in order to achieve a more uniform temperature in that zone. It also contains sufficient catalyst for conducting a complete test. The minimum quantity of catalyst which must be loaded into the tank is the necessary quantity for conducting a test plus a quantity of 10 to 30 g of catalyst serving to maintain a seal between the reactor 4 and the atmosphere of the tank 1a.

The outlet diameter 2, 2a of the tank 1a is important for controlling the flow of solid towards the reactor 4. This diameter determines the interval of catalyst flow that can be achieved. The limits change with the properties of the catalyst, mainly with its apparent density. The flow is regulated with the pressure difference between the tank 1a and the reactor 4. A flow of gas, preferably nitrogen, passes through the line 43 which connects the catalyst tank 1a and the separator 5, and includes the valve 20. This valve 20 originates a load loss which permits the flow of catalyst to be regulated and can be actuated by the central control unit or manually by an operator. The same flow of gas also serves for the separation operation.

The system permits the load loss to be kept constant if the pressure in the separator 5 is changed. Another option consists of using two different flows, one for the pressurisation of the catalyst tank 1a and the other for separation in the separator 5. In that case, the line 43 does not connect with the separator 5 and instead the outlet from the valve 20 is open to the atmosphere.

The pressure difference between the tank 1a and the reactor 4 is preferably controlled continually and is kept constant from the control unit. For example, with an FCC catalyst, of apparent density 1, a pressure difference of between 0 and 0.5 bar and an outlet with a diameter of 1.65 mm, the flow of catalyst can be regulated to between 10 and 120 g/min.

In the case of feeding a liquid reagent, before starting the test the feed starts to flow via the second preheater 11 so that temperature can reach equilibrium; 1 or 2 minutes are usually sufficient for this. The feed used during that time can be recycled or rejected if it is considered that it might have undergone an alteration due to its preheating. The recorded temperature of the second feed can vary between 100 and 400° C., lying between 120 and 300° C.

Described below are some tests conducted in a test unit corresponding to the embodiment shown in FIGS. 1, 2 and 4 to 6.

Test 1: Cracking of Gasoil

The properties of the feed and of the catalyst used are detailed in Tables 1 and 2, respectively. Table 3 summarises the operating conditions. Indicated in Table 4 are the yields by weight of the products with respect to the feed.

TABLE 1

Properties of the feed

| | |
|---|---|
| Density (15° C., g/cm$^3$) | 0.9072 |
| Sulphur (% weight) | 1.4 |
| K UOP | 12.03 |
| Aniline point (° C.) | 91.2 |
| Mean molecular weight (g/mol) | 438 |
| Viscosity (100° C., cst) | 6.29 |
| CCR (% weight) | 0.32 |

| Distillation ASTM 1160 (%) | (° C.) |
|---|---|
| 5 | 331 |
| 10 | 360 |
| 50 | 448 |
| 90 | 539 |

TABLE 2

Properties of the catalyst used

| | |
|---|---|
| Rare earths content | 1% |
| BET surface (m$^2$) | 170 |

TABLE 3

Operating conditions

| | |
|---|---|
| Feed flow (g/min) | 12 |
| Catalyst to feed ratio, CTO | 5.62 |
| Stripping temperature (° C.) | 460 |
| Reaction temperature (° C.) | 510 |
| Estimated residence time of the gas (s) | 0.25 |

The data were obtained in a reactor of 0.5 m in length and 0.9 cm in diameter. Nitrogen is used for the transport of the solid and for atomisation of the load in the reactor, the total quantity of nitrogen in the reactor for each test is 7.8% by weight of the feed. The conversion is the sum of gases, gasoline and coke.

TABLE 4

Yields

| | |
|---|---|
| Conversion | 55.54 |
| Dry gas | 0.68 |
| Propylene | 3.54 |
| Propane | 0.36 |
| Isobutane | 2.33 |
| n-butane | 0.39 |
| C4 olefins | 5.19 |
| Total LPG | 11.81 |
| Gasoline (C5-216° C.) | 40.23 |
| LCO (216-359° C.) | 20.99 |
| 359° C.+ | 23.47 |
| Coke | 2.83 |

Test 2: Cracking of Gasoil

The feed and the catalyst are identical to those of example 1. Other operating conditions are used (Table 5).

TABLE 5

Operating conditions

| | |
|---|---|
| Feed flow (g/min) | 2.5 |
| Catalyst to feed ratio, CTO | 17.04 |
| Stripping temperature (° C.) | 460 |
| Reaction temperature (° C.) | 510 |
| Estimated residence time of the gas (s) | 1 |

TABLE 6

Yields

| | |
|---|---|
| Conversion | 79.77 |
| Dry gas | 1.45 |
| Propylene | 7.44 |
| Propane | 1.22 |
| Isobutane | 7.51 |
| n-butane | 1.24 |
| C4 olefins | 8.02 |
| Total LPG | 25.43 |
| Gasoline (C5-216° C.) | 46.19 |
| LCO (216-359° C.) | 13.29 |
| 359° C.+ | 6.94 |
| Coke | 6.70 |

Test 3: Cracking of Gasoil

The feed and the catalyst are the same as in examples 1 and 2, and the operating conditions are shown in Table 7.

TABLE 7

| Operating conditions | |
| --- | --- |
| Feed flow (g/min) | 8 |
| CTO | 8.78 |
| Stripping temperature (° C.) | 460 |
| Reaction temperature (° C.) | 510 |
| Estimated residence time of the gas (s) | 0.35 |

TABLE 8

| Yields | |
| --- | --- |
| Conversion | 69.68 |
| Dry gas | 0.91 |
| Propylene | 5.41 |
| Propane | 0.76 |
| Isobutane | 4.52 |
| n-butane | 0.79 |
| C4 olefins | 6.89 |
| Total LPG | 18.37 |
| Gasoline (C5-216° C.) | 45.92 |
| LCO (216-359° C.) | 16.61 |
| 359° C.+ | 13.72 |
| Coke | 4.48 |

Test 4: Cracking of N-Octane

The unit presented here was used for cracking of a hydrocarbon such as n-octane, using a commercial FCC catalyst.

TABLE 9

| Properties of the catalyst used | |
| --- | --- |
| Rare earths content | 0.6% |
| BET surface (m$^2$) | 127 |

TABLE 10

| Operating conditions | |
| --- | --- |
| Feed flow (g/min) | 0.5 |
| CTO | 21.14 |
| Stripping temperature (° C.) | 400 |
| Reaction temperature (° C.) | 700 |
| Estimated residence time of the gas (s) | 2.8 |

TABLE 11

| Yields (% feed weight) | |
| --- | --- |
| Conversion | 77.52 |
| Hydrogen | 1.32 |
| Methane | 12.00 |
| Ethane | 9.10 |
| Ethylene | 22.89 |
| Propane | 1.12 |
| Propylene | 15.93 |
| I-butane | 0.25 |
| N-butane | 0.30 |
| T-2-butene | 2.23 |
| 1-butene | 1.96 |
| I-butene | 1.72 |
| C-2 butene | 1.81 |
| C5+ | 4.06 |
| Coke | 2.83 |

Test 5: Selective Oxidation of Propane to Propylene

This time, the feed used in presented unit is gaseous feed. The reagent feed is done with a pellet and a flow meter, which replace the pump-syringe for liquid feed. As the products are all gaseous the liquid trap 6 is not used and all the products are collected in the burette 8.

The catalyst used is a vanadium oxide supported on magnesium oxide.

TABLE 12

| Operating conditions | |
| --- | --- |
| Reaction temperature (° C.) | 570 |
| Stripping temperature (° C.) | 460 |
| Feed flow (m/min) | 80 |
| Flow of inert (m/min) | 120 |
| Estimated residence time of the gas (s) | 3.0 |

TABLE 13

| Yields (molar % of the feed) | |
| --- | --- |
| Conversion | 34.06 |
| distribution of products | |
| Propylene | 35.78 |
| carbon monoxide | 26.49 |
| carbon dioxide | 35.90 |
| methane | 0.48 |
| ethane | 1.34 |

The invention claimed is:

1. A test unit, particularly for the study of catalysts in short contact time reactions between at least one catalyst and at least one reagent, comprising a reactor (4) with at least one load inlet (13, 13a, 13b) for loading a feed consisting of at least one reagent and at least one catalyst which has to intervene in the test reaction, and at least one discharge outlet (14) for the discharge of the catalyst and reaction products resulting from the test reaction, a separator (5) wherein the catalyst is separated from the reaction products, the reactor (5) presenting an admission inlet (15) through which the reaction products and the catalyst gain access to the separator (5), and at least one evacuation outlet for evacuating at least the reaction products separated from the catalyst, and means of heating (1, 11, 17, 17a) for heating at least part of the unit, characterized in that the reactor (4) is a down transported flow reactor, the load inlet (13, 13a, 13b) is arranged in an upper part (4a) of the reactor (4) and the discharge outlet (14) is arranged in a lower part (4b) of the reactor (4), the admission inlet (15) and at least one evacuation outlet (16, 18) are arranged in an upper part of the separator (5), the means of heating (1, 11, 17, 17a) comprise at least a first preheater (1) with at least one tank (1a) housing the catalyst prior to the test reaction for heating the catalyst to the desired temperature before it is loaded into the reactor (4), the first preheater (1) presenting at least one outlet (2, 2a) connected to the load inlet (13, 13a, 13b) of the reactor (4) through a load duct (42) in such a way that, between said outlet (2, 2a) from the first preheater (1, 1a) and said load inlet (13, 13a, 13b) of the reactor (4), some obturator means (3, 3a) are provided which are closed when the catalyst is being heated to the desired catalyst temperature in the first preheater (1) and they open when the catalyst has become heated to the desired catalyst temperature for discharging the catalyst into the reactor (4), the separator (5) is internally divided by a porous element (40) into an upper chamber (39) and a lower chamber (41), the porous element being permeable to gas and impermeable to solid particles of catalyst, said admission inlet (15) being linked with the upper chamber (39), and the discharge outlet (14) from the reactor (4) links with said admission inlet (15).

2. A test unit according to claim 1, characterized in that the first preheater (1) comprises a plurality of tanks (1a) for housing and heating separate catalysts intended for a plurality of tests, the tanks (1a) being connected with said load inlet (13, 13b) to the reactor (4) through the load duct (42), and in that between each tank (1a) and said load inlet (13, 13b) some individual obturator means (3a) are inserted.

3. A test unit according to claim 1, characterized in that the first heater (1) comprises a plurality of tanks (1a) for housing and heating separate catalysts intended for a plurality of tests, the tanks (1a) being connected with said load inlet (13, 13b) to the reactor (4) via an individual load duct (42a), and in that in each individual load duct (42a) some individual obturator means (3a) are inserted.

4. A test unit according to claim 1, characterized in that the obturator means (3, 3a) are conformed in such a way that when they are closed they thermally insulate the first preheater (1) from the reactor (4).

5. A test unit according to claim 1, characterized in that the obturator means (3, 3a) consist of a valve.

6. A test unit according to claim 5, characterized in that the valve is an HT valve.

7. A test unit according to claim 1, characterized in that the reactor (4) is a tubular reactor with a height/diameter ratio of at least 5.

8. A test unit according to claim 7, characterized in that the height/diameter ratio of the reactor (4) is from 50 to 500.

9. A test unit according to claim 1, characterized in that the separator has a diameter greater than the diameter of the reactor (4) and in that the upper chamber (39) of the separator (5) has, above the porous element (40), a height/diameter ratio of 0.2 to 10.

10. A test unit according to claim 9, characterized in that the height/diameter ratio of the separator (5) is from 0.3 to 0.5.

11. A test unit according to claim 9, characterized in that the separator (5) has a diameter from 2 to 100 times greater than the diameter of the reactor (4).

12. A test unit according to claim 9, characterized in that the separator (5) has a diameter from 5 to 15 times greater than the diameter of the reactor (4).

13. A test unit according to claim 1, characterized in that the load inlet (13, 13a, 13b of the reactor (4) comprises
a reagent inlet (13a) which links with a reagent load line (44), and
a catalyst inlet (13b), connected to the catalyst load duct (42, 42a).

14. A test unit according to claim 13, characterized in that the load line (44) is connected through a first end to a load injector (9) for injecting reagents via the reagent inlet (13a) of the reactor (4).

15. A test unit according to claim 14, characterized in that the load injector (9) is further connected to a supply line (49) which conducts an inert gas that is mixed with the reagents before they are loaded into the reactor (4).

16. A test unit according to claim 13, characterized in that is at least one directing valve (12) is inserted in the load line (44), said directing valve permits, in a first position, reagent flow to the reactor (4), and in a second position prevents the entrance of reagent flow to the reactor (4).

17. A test unit according to claim 13, characterized in that the load line (44) comprises a section wherein a second preheater (11) is arranged for heating the reagents before they loaded into the reactor (4).

18. A test unit according to claim 17, characterized in that the second preheater has sufficient heating capacity for heating the reagents to a reaction temperature of between 100 and 400° C.

19. A test unit according to claim 13, characterized in that the load line comprises a second end, away from the reactor (4), connected to a feed pump (10) which pumps the reagents towards the reactor (4).

20. A test unit according to claim 1, characterized in that the outlet (2, 2a) from the first preheater (1) is further connected to a first gas line (45) which conducts a fluidisation gas which fluidises the catalyst before it is loaded into the reactor (4).

21. A test unit according to claim 1, characterized in that the lower chamber (41) of the separator (5) presents a gas access (19) connected to a second gas line (43) which conducts pressurised gas.

22. A test unit according to claim 21, characterized in that the pressurised gas is an inert venting gas.

23. A test unit according to claim 21, characterized in that the gas access (19) is further connected to a third gas line (46) which conducts an oxidising gas.

24. A test unit according to claim 1, characterized in that the first preheater (1, 1a) also has a pressurisation inlet (7) for a pressurisation gas which drives the catalyst towards the reactor (4) when the obturator means (3, 3a) are opened.

25. A test unit according to claim 1, characterized in that it also comprises a gas flow control system (22) which, on the basis of gas pressure values detected by gas pressure measuring means (26, 27, 28, 29), governs gas regulation means (20, 23, 24, 25, 51) inserted in at least one gas conduction line (43, 45, 49), in order to supply under controlled conditions at least one inert gas to the first preheater (1, 1a), to the reactor (4) and/or to the separator (5).

26. A test unit according to claim 24, characterized in that the gas pressure measuring means (26, 27, 28, 29) include at least one pressure meter selected from the group consisting of:
a first pressure meter (26) for measuring first pressures in the first preheater (1, 1a),
a second pressure meter (27) for measuring a pressure difference between a first point in the second gas line (43) conducting fluidisation gas and which connects the first heater (1, 1a) and a gas access (19) in the lower part (5b) of the separator (5),
a third pressure meter (28) for measuring second pressures in the admission inlet (15) to the separator (5), and
a fourth pressure meter (29) for measuring third pressures existing between the second point in the second gas line (43) and the gas inlet (19) for the separator (5),
and in that the gas regulation means (20, 23, 24, 25, 51) comprise at least one regulator means selected from between
a first regulator means (20) provided between said first point and said second point in the second gas line (43), a second regulator means (3) which links the first preheater (1) with the atmosphere, a third regulator means (24) provided in the first gas line (45), a fourth regulator means (25) provided between the second point in the second gas line (43) and the gas inlet (19) to the separator (5), and a fifth regulator means (51) connected to an evacuation outlet (18) from the separator (5).

27. A test unit according to claim 26, characterized in that the third pressure regulating means (23) is a non-return valve.

28. A test unit according to claim 26, characterized in that the gas is an inert gas.

29. A test unit according to claim 28, characterized in that the inert gas is selected from the group consisting of nitrogen, argon and helium.

30. A test unit according to claim 1, characterized in that the first preheater (1, 1*a*) has sufficient heating capacity for heating the catalyst to a temperature of between 100 and 800° C.

31. A test unit according to claim 1, characterized in that the separator (5) is provided with at least one heating element with sufficient heating capacity for maintaining the chambers (39, 41) of the separator (5) at a temperature of between 100 and 600° C.

32. A test unit according to claim 1, characterized in that the heating means also comprise a heating system (17, 17*a*) arranged in the reactor (4) with sufficient heating capacity for maintaining a reaction temperature of between 100 and 700° C. in the reactor (4).

33. A test unit according to claim 32, characterized in that the heating system (17, 17*a*) is adjusted in order to reach the reaction temperature, in accordance with temperature measurements made by at least one temperature sensor (32, 33, 34) selected from the group consisting of a first temperature sensor (32) which measures a first temperature in an upper part (4*a*) of the reactor (4), a second temperature sensor (33) which measures a second temperature in a lower part (4*b*) of the reactor (4), and a third temperature sensor (34) which measures a third temperature in an intermediate part (4*c*) between said upper part (4*a*) and said lower part (4*b*).

34. A test unit according to claim 1, characterized in that the heating system (17) in the reactor (4) comprises sector heating elements (17*a*) with heating capacities adjustable by sectors, in order to maintain the reaction temperature.

35. A test unit according to claim 1, characterized in that the porous element (40) is a porous plate.

* * * * *